(12) United States Patent
Walton et al.

(10) Patent No.: US 7,767,058 B2
(45) Date of Patent: Aug. 3, 2010

(54) NON-WOVEN WET WIPING

(75) Inventors: Richard C. Walton, Boston, MA (US);
Peter R. Smith, Sharon, MA (US);
Drew Horn, Weymouth, MA (US)

(73) Assignee: Micrex Corporation, Walpole, MA (US)

( * ) Notice: Subject to any disclaimer, the term of this patent is extended or adjusted under 35 U.S.C. 154(b) by 357 days.

(21) Appl. No.: 11/688,853

(22) Filed: Mar. 20, 2007

(65) Prior Publication Data

US 2007/0212960 A1   Sep. 13, 2007

Related U.S. Application Data

(63) Continuation of application No. 10/713,900, filed on Nov. 5, 2002, now abandoned, which is a continuation-in-part of application No. PCT/US02/09329, filed on Mar. 26, 2002.

(60) Provisional application No. 60/278,776, filed on Mar. 26, 2001.

(51) Int. Cl.
*B31F 1/12* (2006.01)
*A61F 13/15* (2006.01)

(52) U.S. Cl. ........................ 162/111; 428/152

(58) Field of Classification Search .................. 28/103; 162/111

See application file for complete search history.

(56) References Cited

U.S. PATENT DOCUMENTS

| | | | |
|---|---|---|---|
| 2,915,109 A | 12/1959 | Walton | |
| 3,236,718 A | 2/1966 | Cohen et al. | |
| 3,260,778 A | 7/1966 | Walton | |
| 3,485,706 A | 12/1969 | Evans | |
| 3,679,535 A | 7/1972 | Kalwaites | |
| 3,679,536 A | 7/1972 | Kalwaites | |
| 3,810,280 A | 5/1974 | Walton | |

(Continued)

FOREIGN PATENT DOCUMENTS

GB       2 114 173 A       8/1983

(Continued)

OTHER PUBLICATIONS

Japanese Office Action and English translation dated Oct. 16, 2007 that we received for a related case.

(Continued)

*Primary Examiner*—Lynda Salvatore
(74) *Attorney, Agent, or Firm*—Fish & Richardson P.C.

(57) ABSTRACT

Wet wipe products are made from continuous wet wiping web material having thermoplastic fibers of type, concentration and dispersion capable of being heat-set to set the overall web material in a reformed shape. A succession of ridges and grooves is formed by passing the performed material through a dry creper apparatus in absence of adhesives, the action characterized by pressing the material with a stationary pressing surface to engage an advancing drive surface, the driven material bodily collapsing into a succession of adjacent ridges and grooves that increase the volume of the material. The wet wiping material is heat set in the ridge and groove configuration, enabling the ridge and groove configuration to be preserved when the wet wiping material is wetted and when squeezed and released. The self-restoring ridge and groove configuration provides stress concentrating edges and improves liquid delivery and wet wiping in a number of respects.

24 Claims, 11 Drawing Sheets

U.S. PATENT DOCUMENTS

| | | | |
|---|---|---|---|
| 3,869,768 | A | 3/1975 | Walton et al. |
| 3,975,806 | A | 8/1976 | Walton |
| 4,090,385 | A | 5/1978 | Packard |
| 4,142,278 | A | 3/1979 | Walton et al. |
| 4,286,030 | A | 8/1981 | Moore |
| 4,422,892 | A * | 12/1983 | Plant .......................... 156/209 |
| 4,717,329 | A | 1/1988 | Packard et al. |
| 4,859,169 | A | 8/1989 | Walton et al. |
| 4,894,196 | A | 1/1990 | Walton et al. |
| 5,227,224 | A | 7/1993 | Ishikawa et al. |
| 5,240,764 | A | 8/1993 | Haid et al. |
| 5,254,399 | A | 10/1993 | Oku et al. |
| 5,284,703 | A | 2/1994 | Everhart et al. |
| 5,500,281 | A * | 3/1996 | Srinivasan et al. .......... 428/131 |
| 5,935,880 | A * | 8/1999 | Wang et al. ................... 442/65 |
| 6,315,864 | B2 | 11/2001 | Anderson et al. |
| 6,375,889 | B1 | 4/2002 | Holmes |
| 2002/0150609 | A1 * | 10/2002 | Kono et al. ................. 424/443 |

FOREIGN PATENT DOCUMENTS

| | | |
|---|---|---|
| JP | 01-156570 A | 6/1989 |
| JP | 05-192285 A | 8/1993 |
| JP | 09-067748 A | 3/1997 |
| JP | 10-140454 A | 5/1998 |
| JP | 10-140458 A | 5/1998 |
| JP | 2000-043961 | 2/2000 |

OTHER PUBLICATIONS

*Complex Textiles Glossary*, Calanese Acetate LLC (2001).
*Designing Fabrics for High-Tech Applications*, Occupational Health & Safety Newsletter. Stevens Publishing, www.stevenspublishing.com, printed Mar. 6, 2007.
Flat Blade, *Textiles/Paper/Nonwovens/Heathcare/Service, Softness, Bulk, Shrinkage Control, Stretch, Extensibility, Drape, Hand, Decorative Effects, Absorbancy*. Micrex Corporation (Jul. 1997).
Gupta, V. B., *Heat Setting*. Journal of Applied Polymer Science, vol. 83, pp. 586-609 (2002.
International Search Report issued in WO 2002/076723A1, dated Jul. 8, 2002.
Micrex®/Microcreper—Flat Blade, *Operating Guide Draft*. Micrex Corporation. (Jul. 16, 1997).
*Narrow Fabrics—Glossary of Products*, B2B Online Marketplace for narrow fabrics. http://www,narrow-fabrics-manufacturers.com/glossary-of-products-h.html., printed Mar. 6, 2007.

* cited by examiner

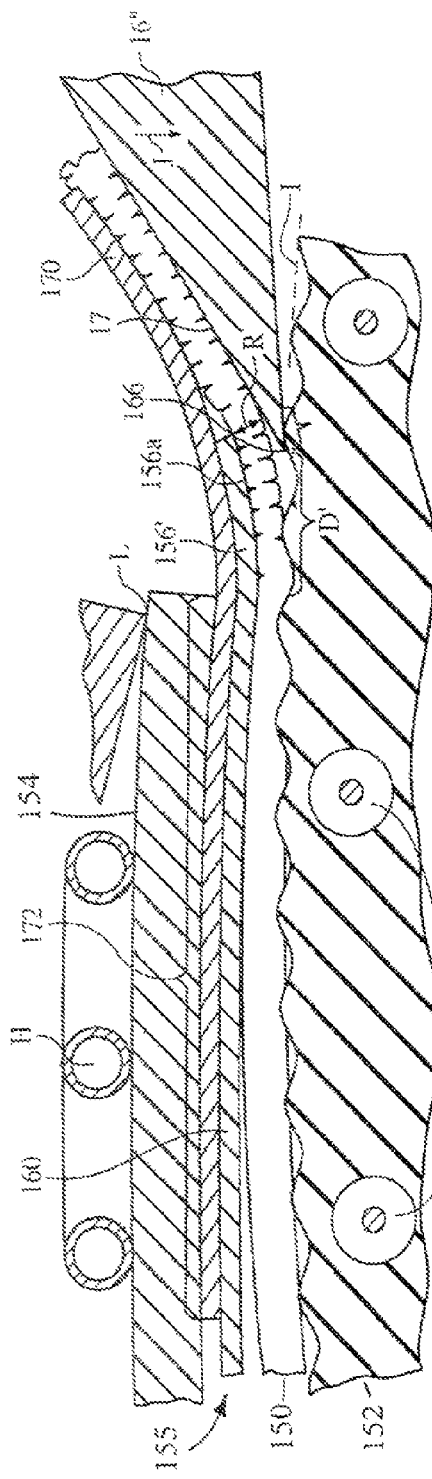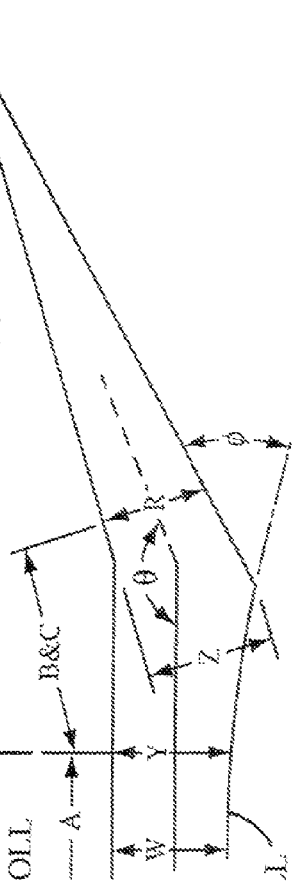
FIG. 12
FIG. 13

NON-WOVEN WET WIPING

This application is a continuation of U.S. patent application Ser. No. 10/713,900 filed Nov. 5, 2002, now abandoned published as U.S. 2004/0161991 A-1, which is a continuation in part of International Application PCT/US02/09329, filed Mar. 26, 2002, which claims priority to U.S. patent application Ser. No. 60/278,776 filed Mar. 26, 2001. The entire contents of U.S. 2004/0161991 are hereby incorporated by reference.

TECHNICAL FIELD

This invention relates to non-woven wiping sheets and in particular to so-called "wet wipes", i.e. sheets that are pre-wet with a desired wiping fluid and sold in a fluid tight container, and sheets that, though packaged dry, are adapted to be wetted or significantly moistened by the user.

BACKGROUND

Wet wipes are typically non-woven materials made of a combination of synthetic strength fibers and absorbent or adsorbent fibers, which are usually cellulosic fibers such as wood pulp.

In other cases the strength fibers are cotton, rayon or other cellulosic fibers.

While useful in many instances, present-day wet wipes may not have the most desirable appearance; they may present considerable drag to being drawn across a surface being wiped; their wiping ability is not as good as may be desired. Their fluid holding, fluid releasing and fluid re-imbibing properties may not be as good as desired.

In general improved wet wipes would increase their use and convenience.

SUMMARY

According to one aspect of invention, a method for manufacturing an improved wet wipe product is provided comprising:

providing a continuous, preformed, nonwoven self-supporting sheet-form wet wiping web material constructed for a predetermined wet wiping task, at least 20% by weight of the wet wiping material comprising thermoplastic fibers, the thermoplastic fibers being of type, concentration and dispersion selected to be capable of being heat-set when the material is in a reformed shape to set the thermoplastic fibers and thereby the overall web material in the reformed shape, forming, by dry creeping action, a succession of ridges and grooves in the preformed wet wiping material by passing the material through a dry creper apparatus in the absence of an adhesive agent, the action characterized by pressing against one side of the material with a stationary pressing surface, to cause the opposite side of the material to engage with an advancing drive surface in the absence of adhesion to the advancing surface, and thereby driving the sheet material forward against previously dry creped material which has been retarded, to cause bodily collapse of the material into a succession of adjacent ridges and grooves that increase the volume of the overall material, heating the wet wiping material to a temperature and in a manner sufficient to heat-set the dry-creped thermoplastic fibers and thereby the ridge and groove configuration of the overall material to enable the ridges and groove configuration to be preserved when the wet wiping material is wetted, and thereafter fabricating the continuous wet wiping material with its heat-set ridges and grooves into a series of wipe member for individual use.

"Dry-creping" referred to her means creping a preformed web, without the web being adhesively adhered to a surface (as in a Yankee dryer) and does not preclude the addition of limited moisture during the process, as by adding a modicum of steam to the web to soften fibers to facilitate the dry-creping action.

Preferred embodiments of this method have one or more of the following features:

The preformed web material is selected to comprise between about ⅓ and ⅔ by weight of the thermoplastic fibers.

The thermoplastic fibers comprise PET (polyester).

The thermoplastic fibers comprise polypropylene.

The thermoplastic fibers comprise polyethylene.

The sheet-form web material is comprised substantially entirely of thermoplastic fibers.

The preformed web material is selected to include a substantial quantity of wettable fibers in an assemblage having substantial wicking capability, and the process is conducted in manner whereby the heat-set of the ridge and groove configuration enhances the recoverable internal volume of the wipe members.

The preformed web material is selected to include at least about ⅓ by weight of liquid absorbent or liquid adsorbent fibers. In preferred forms, the absorbent or adsorbent fibers are cellulosic, e.g. natural fibers or rayon.

The preformed web material comprises fibers of PET and fibers of wood pulp.

The preformed web material comprises a fiber assemblage which includes a substantial proportion of wood pulp fibers, the fiber assemblage is substantially free of thermoplastic binder, and the dry-creping is conducted in a manner leaving the wood pulp fibers substantially permanently uncompressed in the direction of the thickness of the assemblage.

The preformed web material comprises a spunlace web. In a preferred case, the preformed spunlace web is formed by providing a carded web of polyester fibers, introducing a layer of wood pulp to the carded web, and subjecting the layer of wood pulp and carded web to hydroentanglement followed by dewatering and drying to form a self-supporting sheet-form web material for introduction to the dry-creping.

The preformed web material is fabricated at least in part by the process of thermal bonding, chemical bonding, spun bonding, melt blowing, caustic entangling, hydraulically aperturing, hydro-entangling, wet laying or papermaking.

In preferred embodiments the sheet coarsely dry-creped, and the resultant coarse ridges in the fabric contribute to enhanced performance.

By "coarse" in reference to the ridge and groove formations imparted to the sheet member by dry, coarse creping while heat-setting, is meant a ridge and groove pattern that, rather than being microscopic or virtually invisible, is sensibly prominent, in general, comprising fewer than about 25 ridges per lineal inch.

Within this parameter, very important further characteristics can be obtained with many webs by the coarse formations. The desirable effects obtained depend upon the type of desired wipe action.

Preferred embodiments of the method have one or more of the following features:

The method is conducted in the manner to form the ridges at frequency between about 8 and 25 ridges per lineal inch the method is conducted in the manner to form ridges defining wipe-stress concentrating edges at frequency between about 8 and 15 ridges per lineal inch, useful, for instance, for vigorous wiping action.

The method is conducted in the manner to form ridges defining wipe-stress concentrating edges at frequency between about 15 and 20 ridges per lineal inch, useful, for instance, for moderating wiping action.

The method includes stacking a series of wet wipe members face-to-face in a stack, with substantial non-alignment between ridges and grooves in successive members in the stack.

When inserting the stack into a package, in a preferred instance, the package is liquid tight and a liquid agent is included with the wet wipe members in the package. In certain cases the liquid agent comprises at least one of a soap, a detergent, a solvent, a cleaning agent, a window washing agent, a sanitizing agent, a biocide, a polishing agent, an abrading agent or a neutralizing agent. In other cases the liquid agent comprises at least one of an insect repellant, a pain solvent, a paint remover, a finish remover, an oil solvent, a grease solvent, a cosmetic remover, a makeup remover, a stain remover, a stain, a paint, a varnish, a wax or a polish.

Further aspects of invention concern novel product produced by the foregoing methods.

In one instance a non-woven wet wipe product produced by the method comprises at least one sheet member, pre-wetted with a wet wiping agent, and disposed in a fluid-proof package, the product comprising:

a. a segment of a non-woven self-supporting sheet-form wet wiping web material comprised of an assemblage of hydroentangled fibers including synthetic thermoplastic strength-providing fibers and absorbent or adsorbent fibers, b. the non-woven material being in a permanent, dry-creped, heat-set condition defining a succession of ridges and grooves in the overall body of the material, the constituent thermoplastic fibers of the sheet member having been heat-set during the imparting of the ridges and grooves to the material, the heat-set condition of the dry-creped thermoplastic fibers preserving the ridge and groove configuration during prolonged presence in the material of the wet agent, c. the wet wiping agent being disposed through the body and on the surface of the dry-creped, heat-set sheet form member and its constituent fibers.

In another instance a non-woven wet wipe product produced by the method comprises at least one adsorbent sheet member adapted to be wetted with a wet wiping agent, the product comprising:

a. a segment of a non-woven self-supporting sheet-form wet wiping web material comprised of an assemblage of fibers, that includes synthetic thermoplastic fibers, b. the non-woven material being in a permanent, dry-creped, heat-set, volume-enhanced condition, the constituent thermoplastic fibers of the sheet member having been heat-set during the creping of the material, the heat-set condition of the dry-creped thermoplastic fibers capable of preserving the volume-enhanced structure of the assemblage during prolonged presence in the material of the wet wiping agent.

In important cases, the invention pertains to wet wipes, which may be either pre-wetted or sold dry to wetted by the user, that are formed of nonwoven starting materials that may employ a great variety of fibers typically having adsorbent and wicking characteristics, while at least 20% of the fibers in the assembly being thermoplastic and capable of being heat set. The starting web materials can be made via a variety of nonwoven manufacturing processes including thermal bonding, chemical bonding, spunbonding, meltblowing, caustic entangling, hydraulically aperturing, wet laying, papermaking and combinations of these method. In some advantageous cases, hydroentanglement is employed to provide fiber entanglement and coherency of the web. In other cases, other fiber entanglement or bonding or adhering processes are employed to form a coherent web preform. Such web preforms, however made, are then processed according to the present invention, by being dry-creped under heating conditions that heat set the creped thermoplastic fibers to produce a volume enhanced structure. These materials are process to provide pre-wet wiped in fluid tight containers and wipes that are designed for use after the user wets them, being packaged dry in a package that may or may not be fluid tight.

As previously indicated, with wet wipes for which a vigorous wiping action is desired, it is advantageous to employ a gross coarse crepe, i.e. the heat set ridge frequency is between about 8 and 15 per lineal inch. The resultant strongly pronounced ridges effectively provide wipe-stress-concentrating edges that enable high wiping pressure (pounds per square inch) to be applied to the edges (the entire wiping force thus being distributed over a relatively low aggregate length of relatively sharp edges). Further, the heat-set gross coarse dry crepe can contribute significant overall thickness to a single wipe, and, because of the relative randomness of ridges in one wipe sheet in a stack relative to the next, arising because of the absence of complete regularity in the ridge pattern inherent with creping, the sheets are prevented from nesting, contributing significantly to the space occupied by a single wipe in a stack of wipes. The crepe ridges and grooves thus increase the fluid-carrying capacity of the individual wipes, which is important where a significant flood of the wet wiping agent is required.

In important embodiments, the creping with heat set increases the recoverable internal volume of the nonwoven fabric. By "recoverable volume" is meant, that, after being squeezed to deliver liquid, and then released, the liquid carrying volume is recoverable, i.e. the web swells by itself, or when it imbibes liquid, its internal volume swells, so that a significant volume of the liquid is retained. This recoverable volume characteristic of the heat set, dry creped product increases the ability of the wipe material to adsorb liquids. Further, to the degree the adsorption is increased, it is important to note that the reciprocal ability to desorb liquids is increased. Thus a treated wipe can adsorb a liquid, then when squeezed or subjected to wipe pressure, it can desorb to deliver the liquid to the surface being wiped, subsequent to which it can resorb the liquid to remove liquid along with picked-up contaminant from the wiped surface. Both sorbing and desorbing characteristics of the web are increased by the dry creped, heat set thermoplastic network of fibers in assemblies that have wettable fibers with appropriate wicking capability. In important embodiments, the aggregate interstitial space between adjacent fibers, and accordingly the overall internal volume of the wipe, is increased by the heat set creping. The treatment enables improved liquid adsorption, desorption and resorption, likened to an effective pumping action, with respective relaxation, compression, and relaxation of compressive action of the user upon the surface being wiped.

Therefore an important aspect of invention is heat-set of the ridge and groove configuration in the overall body of the material that preserves the configuration during presence in the material of the wet agent and after being squeezed by the user to deliver liquid and then released.

With wet wipes for which a moderate wiping action is desired, according to the invention it is readily possible to tailor the conditions of treatment to produce moderately coarse formations, i.e. between about 15 and 20 heat-set ridges per lineal inch. Again there is obtained the stack thickness-enhancing effect of non-alignment of ridges in successive layers of a stack, and significantly enhanced thickness and fluid-carrying capacity to the individual wet wipe sheet. The greater density of ridges spreads the wiping force over a longer aggregate ridge length, producing lower, but still significant contact pressure at the ridge edges.

For cosmetic use, baby care and other uses in which gentle action is desired, minimally coarse ridges, i.e. between about 20 to 25 ridges per lineal inch, provide the possibility of a relatively gentle wiping action while still obtaining, to a reduced degree, the thickening and liquid-capacity enhancing advantages of the invention.

There are case where even a finer distribution of the heat-set dry crepe formations in the wet wipe may be employed, as well, e.g. for hypersensitive skin use. In some examples of hydroentangled and other web structures, the crepe pattern is selected to be so fine that it is hard to detect visually without magnification, but the physical changes in internal volume, stretch at break, thickness and liquid capacity will be apparent, all provided by the heat set thermoplastic crepe structure.

Another feature of the invention, which is important, e.g., for the vigorous and moderate action wipes, is the effect obtained in wiping a smooth surface such as glass or metal plate, or other continuous surface. This has to do with a vacuum-release effect achieved by the permanent fluid-resistant ridge and groove structure, which is particularly noteworthy when employing gross coarse crepes heat-set in the wet wipe. Despite the sheet member having a high fluid-carrying capacity, it is found, during use, that the troughs of the sheet are not completely fluid-filled, i.e. continuous air channels are preserved between adjacent ridges, which communicate with ambient. These air channels are partially retained in the pre-wet sheet even when significant wipe pressure is exerted. Relatively smooth wet wipe sheets (i.e. sheets not having features of the present invention) when pressed against a flat surface being wiped, give up entrapped air at the interface and then tend to be forced, by ambient air pressure, bodily against the surface being wiped. According to the present invention it is realized that this pressure adds to frictional resistance to lateral movement of the wipe sheet across the work surface, increasing the effort required, by the worker. The coarse creped, heat-set ridges and grooves of wet wipes of the present invention, on the other hand, while achieving improved concentration of wipe pressure at the working ridges, are formed to effectively reduce the total wiping effort required, believed to be due to the presentation of the vacuum-releasing air channels.

Another feature is that heat set creped wipes that have the low overall cohesion with the surface being wiped need not be subject to much distortion by forces applied during wiping. As a result, the liquid carried is not prematurely discharged, and thus the user is given good control over the release and recovery of the solvent or washing liquid.

Accordingly, in preferred embodiments of the invention, the wet wipe product has between about 8 to 25 heat-set dry crepe ridges per lineal inch of the web. For vigorous wiping action, the wet wipe product has between about 8 and 15 heat-set dry crepe ridges per lineal inch of the web, for moderate wiping action, the wet wipe product has between about 15 and 20 heat-set dry crepe ridges per lineal inch of the web, while for fine or gentle wiping action, the wet wipe product has between about 20 and 25 heat-set dry crepe ridges per lineal inch of the web.

In another aspect, the invention provides a non-woven wet wipe product including a sheet member, pre-wetted with a wet wiping agent, and disposed in a fluid-proof package, the product including a segment of a non-woven self-supporting web made up of an assemblage of hydroentangled fibers including synthetic thermoplastic strength-providing fibers and absorbent or adsorbent fibers. The non-woven web is in a permanent, dry-creped, heat-set condition defining a succession of ridges and grooves in the overall body of the web, the constituent thermoplastic fibers of the sheet member having been heat-set during the imparting of the ridges and grooves to the web. The heat-set condition of the dry-creped thermoplastic fibers preserve the ridge and groove configuration during prolonged presence in the web of the wet agent. The wet wiping agent is disposed through the body and on the surface of the dry-creped, heat-set sheet-form member and its constituent fibers. As before, in preferred instances the sheet is coarsely dry-creped, resulting in a coarse distribution of ridge formations in the sheet. For instance there are between about 8 and 25 heat-set ridges per lineal inch of the web (between about 3.1 and 9.8 ridges per linear cm), or between about 8 and 15 heat-set ridges per lineal inch of the web (between about 3.1 and 5.9 ridges per lineal cm), or are between about 15 and 20 heat-set ridges per lineal inch of the web (between about 5.9 and 7.9 ridges per lineal cm), or between about 20 and 25 heat-set ridges (24) per lineal inch of the web (between about 7.9 and 9.8 ridges per lineal cm).

These and other described aspects of the invention can include one or more of the following features. The sheet member is made up of between about ⅓ and ⅔ by weight absorbent or adsorbent fibers and between about ⅓ and ⅔ by weight of synthetic thermoplastic, strength-imparting fibers. The sheet member comprises about equal weight of the absorbent or adsorbent fibers and the thermoplastic which may be strength providing. The thermoplastic fibers include PET (polyester). The thermoplastic fibers include polypropylene. The thermoplastic fibers include polyethylene. The absorbent or adsorbent fibers are cellulosic. The cellulosic fibers are natural fibers. The absorbent or adsorbent fibers include rayon. The wet wipe product includes fibers of PET and fibers of wood pulp. As in the case of wipes for use with alcohol, the nonwoven can be made entirely of adsorbent fibers, e.g. thermoplastic fibers, and not contain any absorbent fibers. The pre-form web from which the wet wipe product is made is a spunlace web. Other embodiments include all the types of nonwovens previously mentioned above, including wet laid products.

The wet wiping agent is, at least partially, an aqueous agent. The wet wiping agent includes a soap, a detergent, a solvent, a cleaning, a window washing, a sanitizing, a biociding, a polishing, an abrading and/or a neutralizing agent. The wet wiping agent includes an insect repellant, a paint solvent, a paint remover, a finish remover, an oil solvent, a grease solvent, a cosmetic remover, a makeup remover, a stain remover, a stain, a paint, a varnish, a wax and/or a polish. The wet wiping agent is a liquid that does not include water such as hydrocarbon solvent, nonaqueous coatings, and the like or the wipe is made to adsorb and pick-up such liquids.

In another aspect, the invention provides a package containing a face-to-face stack of a plurality of sheet members, each sheet member being a segment of a non-woven self-supporting web made up of fiber assemblage, e.g., of hydroentangled fibers, including synthetic thermoplastic strength-providing fibers and absorbent or adsorbent fibers. The non-woven web is in a permanent, dry-creped, heat-set condition defining a succession of ridges and grooves in the overall body of the web, the constituent thermoplastic fibers of the sheet member having been heat-set during the imparting of the ridges and grooves to the web. The heat-set condition of the dry-creped thermoplastic fibers preserves the ridge and groove configuration during prolonged presence in the web of the wet agent. The wet wiping agent is disposed through the body and on the surface of the dry-creped, heat-set sheet-form member and its constituent fibers.

This aspect of the invention can include any one or more of the features discussed above with reference to the other aspects of the invention.

In another aspect, the invention provides a method of producing a wet wipe product including providing a self-supporting non-woven assemblage of e.g., hydroentangled fibers including synthetic thermoplastic fibers which may be strength-providing and absorbent or adsorbent fibers; passing the non-woven assemblage through a dry-creping machine to impart ridges and grooves to a body of the assemblage while simultaneously heating the assemblage to a temperature above the temperature required to heat-set the thermoplastic fibers; and, thereafter, sizing the assemblage into a wipe member, pre-applying a wet wiping agent so that the wet wiping agent is disposed through the body and on the surface of the dry-creped sheet-form member and it constituent fibers, and sealing the wipe member in a fluid-tight package, or packaging the wipe dry to be wetted by the user.

This aspect of the invention can include any one or more of the following additional features. The dry-creping is performed under conditions to produce coarse dry-crepe. A spunlace process is employed for providing the nonwoven assemblage. The assemblage is formed by providing a carded web of polyester fibers, introducing a layer of wood pulp to the carded web, and subjecting the layer of wood pulp and the carded web to hydroentanglement followed by dewatering and drying prior to dry-creping. The method includes conducting the dry-creping step with a bladed drycreper including a driven roll and a pressing surface for pressing the fiber assemblage against the driven roll sufficiently to cause the fiber assemblage to be advanced forward, and opposing the advance of the assemblage in the direction of the plane of the assemblage with a retarder blade, a tip of which is held adjacent the driven roll, at least one surface of the drycreper being heated to heat the thermoplastic fiber constituent to heat-set temperature of the thermoplastic fibers. The absorbent or adsorbent fibers include wood pulp fibers, the fiber assemblage is substantially free of thermoplastic binder, and the dry-creping is conducted in a manner leaving the wood pulp fibers substantially permanently uncompressed in the direction of the thickness of the assemblage.

In many cases of webs that contain wood pulp, melt blown, and other very small fibers, as a result of heat and pressure caused by their nonwoven manufacturing process, the fibers become closely packed together. Such action can induce detrimental hydrogen bonding and inelastic densification of the fiber mass. The creping with heat set described here serves to increase the space between such small fibers, thus increasing internal volume of the web, and the adsorbent capacity and rate of wetting of wipes produced from the web.

In some embodiments the thermoplastic fibers include PET (polyester) and the surface of the drycreper is heated to a temperature between about 250 and 350 F (139 C and 194 C). In other embodiments of process conditions, roll temperatures may be higher (e.g. to accomplish greater speed, and to drive off moisture to enable the fibers to reach heat set temperature more quickly) or lower (e.g. if the heat of friction provides additional heating of fibers.)

Preferred embodiments have one or more of the following features. The pressing surface and/or the driven roll are heated. The dry-creping and simultaneous heat setting is carried out under conditions in which the absorbent or adsorbent fibers are substantially uncompressed in a direction of thickness of the web during formation of the dry-crepe. The driven roll of the drycreper includes a continuous cylinder, the roll being equipped with an internal heater (H'). The internal heater (H') employs an electric resistance heater. The internal heater (H') includes heat exchange passages through which a hot fluid is passed. The hot fluid is hot water, steam, hot gas, hot air or combustion gas, or oil. The dry-creping and simultaneous heat-setting is conducted in a manner to shorten the web at least 4%, increasing bulk thickness of the sheet member. The dry-creping and simultaneous heat-setting is conducted in a manner to shorten the web within the range between about 4 to 25%. The dry-creping and simultaneous heat-setting is carried out to provide shortening between about 4 and 12%. The dry-creping and simultaneous heat-setting is carried out to provide shortening between about 4 and 8%. A plurality of the sheet members, in a stack and in face-to-face contact, are packaged wet in a fluid tight container. The method includes adding to the sheet members before completing the packaging a soap, a detergent, a solvent, a cleaning, a window washing, a sanitizing, a biociding, a polishing, an abrading and/or a neutralizing agent. The method includes adding to the sheet members before completing the packaging an insect repallant, a paint solvent, a paint remover, a finish remover, an oil solvent, a grease solvent, a cosmetic remover, a makeup remover, a stain remover, a stain, a paint, a varnish, a wax and/or a polish. In other cases the wipes are dry packed and wetted by the user.

In the spirit of this invention it is understood that heating the nonwoven web for accomplishing the heat set of the crepe can be accomplished in a variety of ways. Rollers may be used to conduct heat to the web prior to creping, the rollers heated e.g. by electrical resistance or radiant heat or hot oil. The nonwoven web can also be heated using radiant energy, hot air or a variety of other well known methods to set previously imparted crepe.

The details of embodiments of the invention are set forth in the accompanying drawings and the description below. Other features, objects, and advantages of the invention will be apparent from the description and drawings, and from the claims.

DESCRIPTION OF DRAWINGS

FIG. 6 is a diagrammatic view of one preferred method of forming a pre-form product of hydroentangled fibers while

FIG. 8 and FIG. 9 are perspective illustrations of a preferred drycreper machine from different points of view, while

FIG. 12 is a view similar to FIG. 10 of a gross creping action.

FIG. 13 is a diagram of the conformation of the dry-creping cavity through which the material is passed.

FIG. 14 shows a thickness-measuring device measuring a stack of untreated sheets while

DETAILED DESCRIPTION

Figure 1:
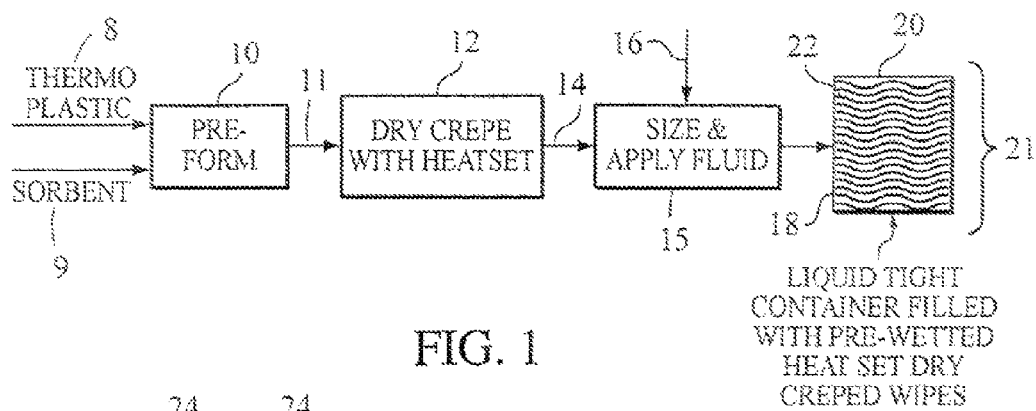
FIG. 1 is a flow diagram of the new process of the invention.

Referring to FIG. 1 a composite web is formed to provide a pre-form web 11 for manufacture of the product. The constituents of the pre-form are thermoplastic strength-providing fibers 8, presently preferred fibers containing PET, and fibers of sorbent material 9, presently preferred hygroscopic wood pulp. The percentage by weight of absorbent or adsorbent fibers 9 of preform 11 is between about ⅓ and ⅔ while the percentage by weight of thermoplastic fibers is about within this same range. In some instances the percentages by weight of absorbent or adsorbent fibers 9 is bout equal to that thermoplastic fibers 8. The fibers are introduced to a machine 10 of suitable construction for providing the pre-formed web 11, i.e., an assemblage of fibers, having structural elements throughout the composite with which are interspersed fine sorbent fibers.

A minimum of about 20% heat settable thermoplastic fibers is required, for enabling formation of the permanent creped structure that restores the internal, adsorbent volume of the wipe when pressure on the wipe is released. Other constituents of the web are selectable based on the particular task and the nature of the liquids expected to be sorbed or desorbed by the wet wipe.

The pre-form sheet 11 is introduced to a drycreper machine 12 which is characterized by its application of heat to the pre-form just before or during the dry-creping process. The applied heat is of a level sufficient, under creping conditions, to heat-set the thermoplastic strength-providing fibers to establish permanence of the crepe configuration under prolonged wet conditions. Following the dry-creping apparatus 12, the dry-creped sheet 14 is introduced to an apparatus 15 that performs a sizing process and introduces a wiping fluid 16 to the substrate as by spraying, immersion or flooding. Either before or after application of wiping fluid 16, the sheet is cut to size and introduced to a container 18 which is sealed by a top 20, the container containing a multiplicity, e.g., a stack 21, of individual layers 22 each containing the wiping fluid 16. These resultant wet wipes 22 are ready for use by the consumer in a one-step process to perform the desired action, for instance a cleaning action, a polishing action, a dusting action or the application of a fluid to a surface.

Figure 2:
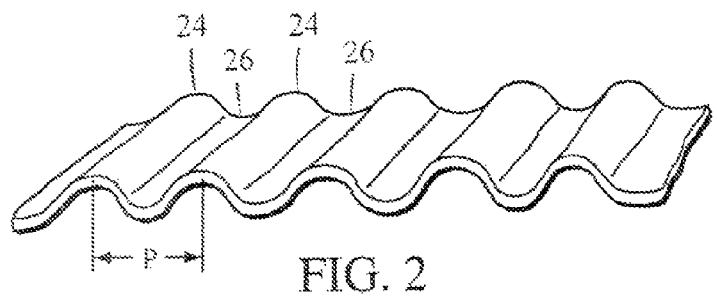
FIG. 2 is a magnified view of a pre-moistened wipe produced by the process of FIG. 1.

Referring to FIG. 2, an individual layer 22 from container 18 has a selected creped configuration such as, for instance, the crepe undulations as shown. The ridges 24 and grooves 26 in the pattern are not precisely identical, one to the next, due to the slightly random or statistical nature of dry-creping, which is based on columnar collapse of successive segments of the web as the driving forces are opposed by retarding forces. Due to slight variations in the thickness, fiber orientation, or fiber concentration in adjacent increments of the web, the crepe repeat length, P, varies slightly in adjacent ridge and groove formations. Because of the randomness of the ridge and groove location on each sheet, adjacent layers 22 within package 18 are highly unlikely to "nest" together. This phenomenon reduces the likelihood that adjacent sheets will cling to one another and helps to ensure that a single wipe can be removed without "pull along," e.g., by friction or adhesion, of a directly subjacent wipe.

Figure 3:
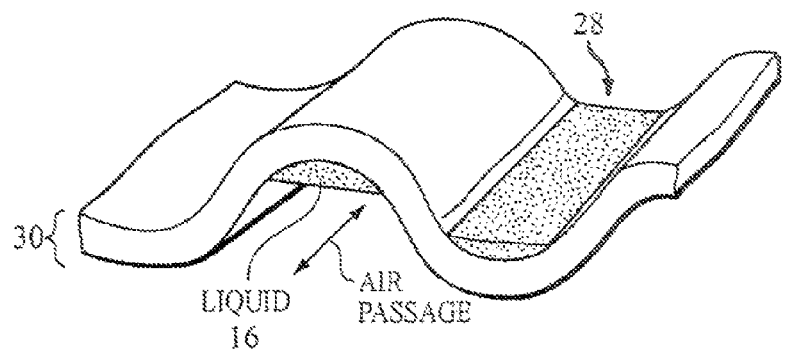
FIGS. 3 and 4 are successively magnified diagrammatic views of a portion of the product of FIG. 2.
Figure 4:
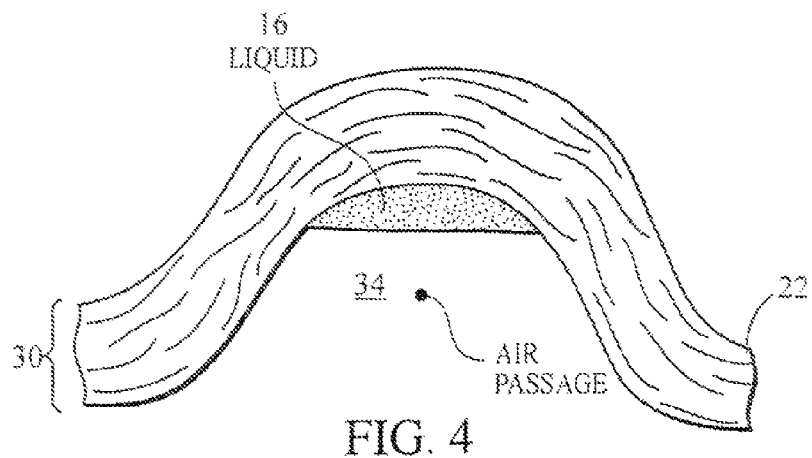

Depicted in FIG. 3 are pockets 28 of fluid 16 contained in crevices formed by the dry-crepe ridges 24 and grooves 26 as well as within the body 30 of the dry-creped fabric. The further magnified view of FIG. 4 illustrates better that quantities of fluid 16 are trapped within the interstices of the substance of the layer 22 and in the conformations provided by the dry-crepe that has been heat-set. Illustrated also in FIGS. 3 and 4 are continuous regions 34 of air in the channels or troughs of the pre-wet sheet. These channels communicate with ambient air.

FIG. 4 depicts, diagrammatically, that the thermoplastic fibers in their heat-set condition, form the web as a whole into the permanent crepes, with absorbent fibers also being a constituent of the web. Again, the aggregations of moisture 16 are depicted, it being also understood that a large percentage of the moisture can be imbibed in the body 30 of fibers of the absorbent pulp or other hygroscopic component of the web.

Figure 5:
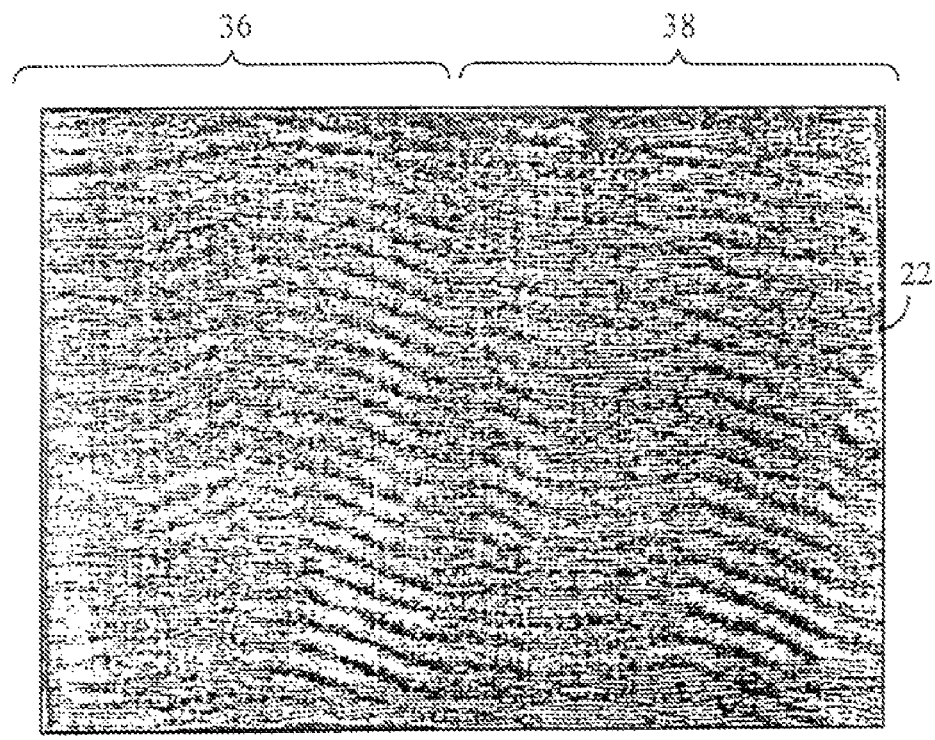
FIGS. 5, 5A, 5B and 5C are photo views of the faces of selected preferred embodiments of the product of the invention prior to application of the moistening agent.
Figure 5A:
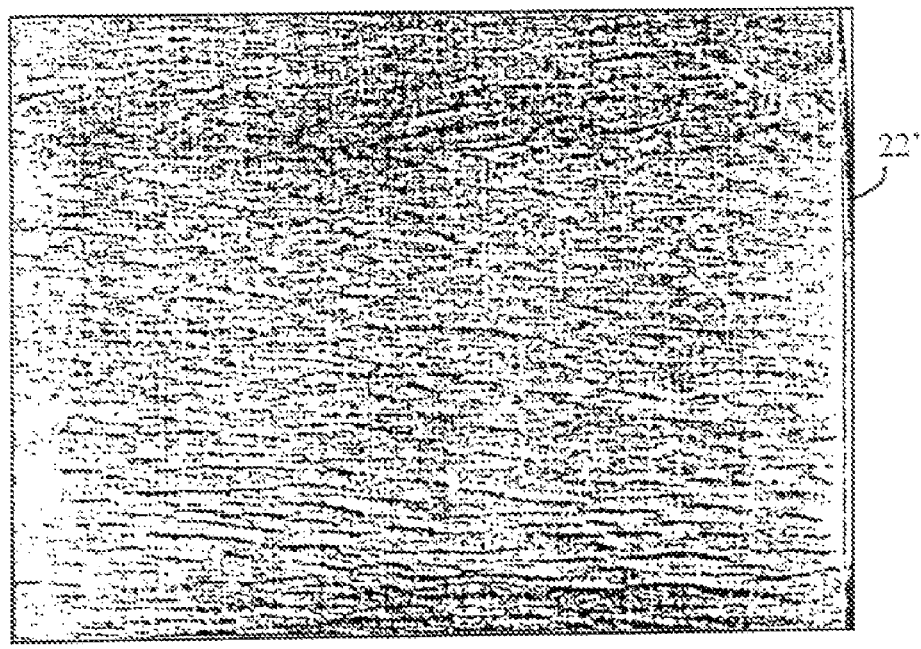
Figure 5B:
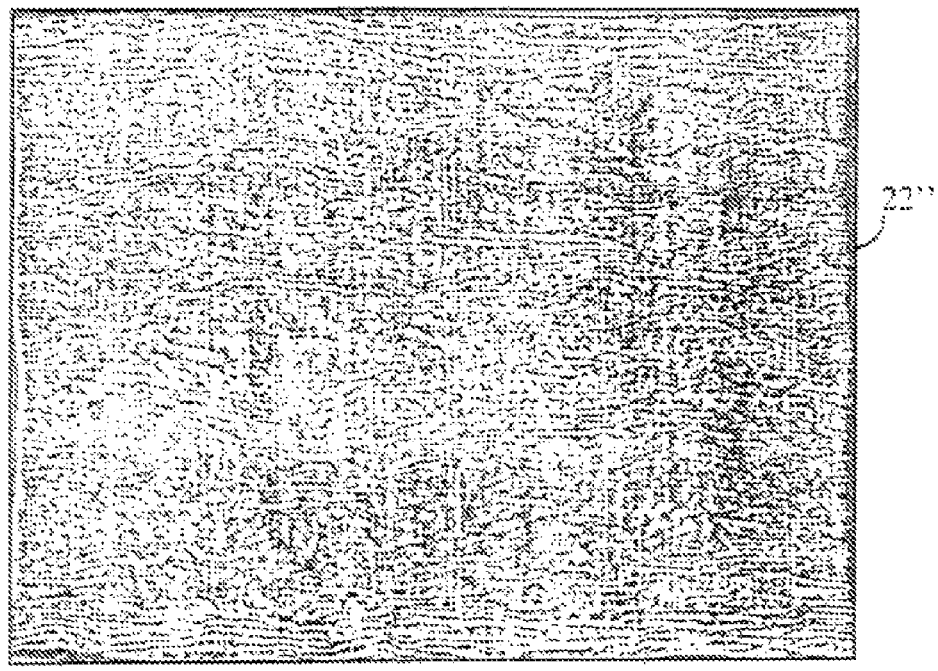
Figure 5C:
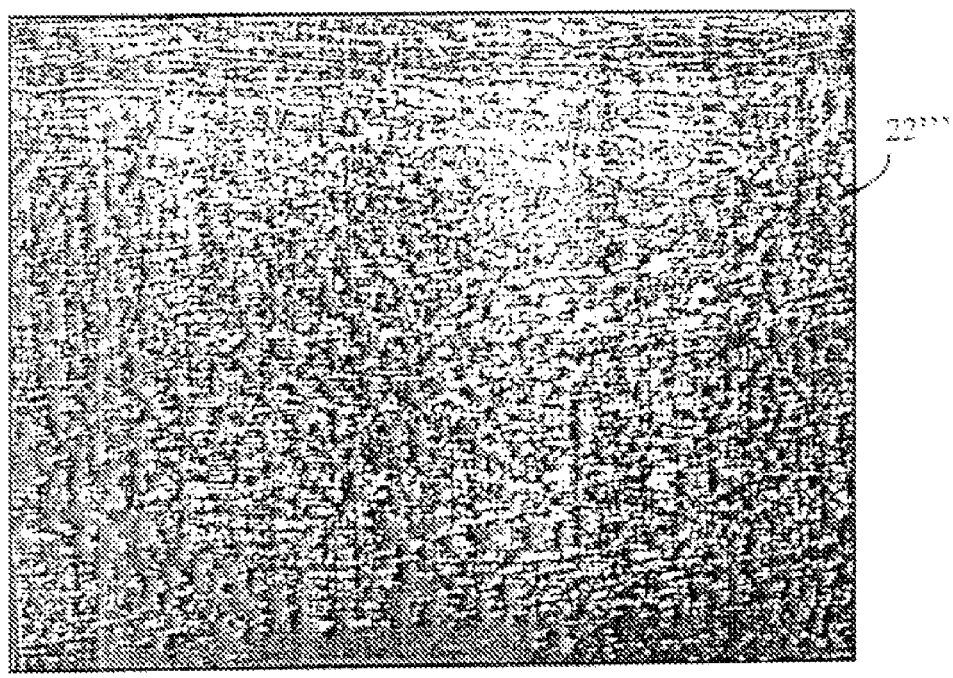

Referring to FIG. 5, the somewhat random distribution of ridges from one region, e.g., region 36, of a sheet 22 to another, e.g., region 38, is clearly seen. Referring now also to FIGS. 5A-5C, sheets 22, 22', 22" and 22''' illustrate the varying degrees of coarse dry-crepe that are achievable, such varying degrees being suitable for customizing a wet wipe to different particular applications. As an example, an infant care wipe or a cosmetic wipe may have the finer heat-set crepes of sheet 22''' (FIG. 5C), with ridges at density of the order of 20 to 25 per lineal inch, while a wipe suitable for window cleaning, dusting, or wiping of machinery may have the grossly coarse configuration of sheet 22 (FIG. 5), with ridge density between about 8 and 15 ridges per inch. Sheets 22' and 22" (FIGS. 5A and 5B, respectively) illustrate intermediate products. The crepe frequency is easily selectable by the setting of the drycreper machine 14 (FIG. 1) to tailor the conformation of the fabric to the type of wiping agent that is to be added for the pre-moistened wipe product desired.

In the presently preferred embodiment, the step 10 (FIG. 1) of pre-forming the web is performed employing the spunlace process that is well known. That process involves hydroentanglement of fibers, such as generally described in the early patents of DuPont, for instance U.S. Pat. No. 3,485,706, and in early patents of Chicopee Mills, for instance U.S. Pat. Nos. 3,679,535 and 3,679,536 and the many later patents in the field which make reference to these early patents. For instance, the reader is referred to U.S. Pat. Nos. 5,240,764; 5,254,399; 5,227,224 and 5,284,703. Another example is UK Patent Publication 2 114 173A.

Figure 6:
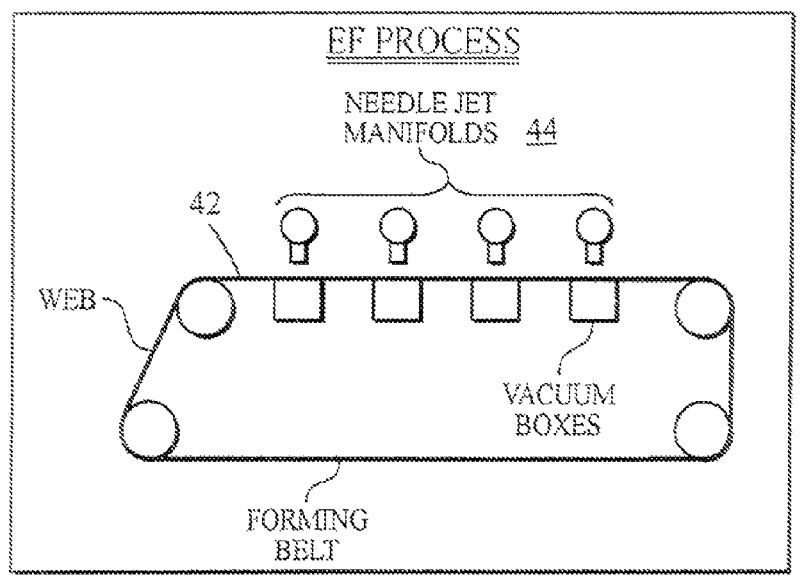
Figure 6A:
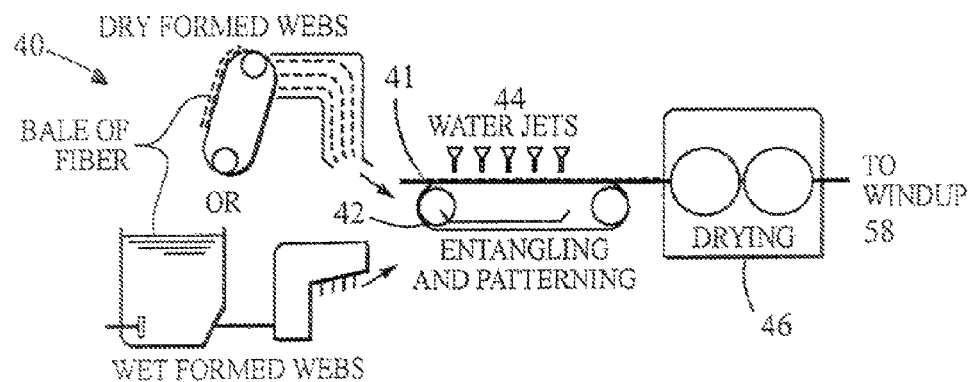
FIGS. 6A-6E are diagrammatic views of complete machines for forming hydroentangled pre-form products.
Figure 6B:
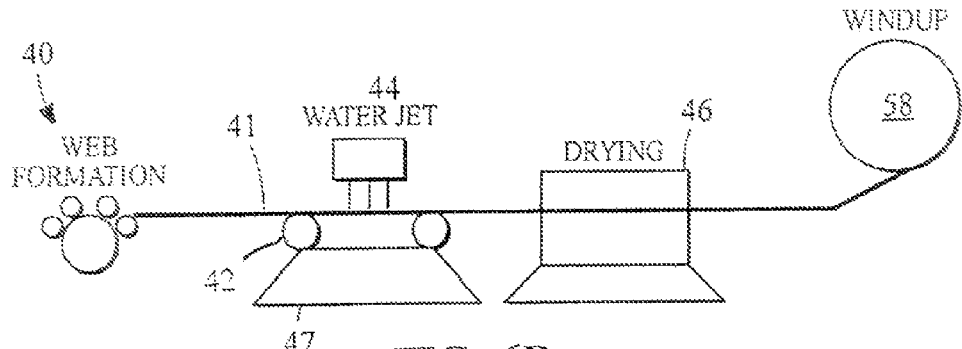
Figure 6C:
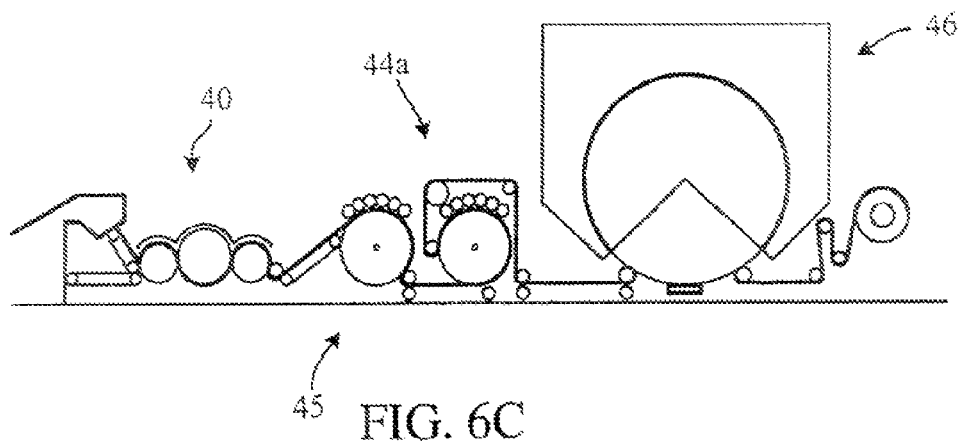
Figure 6D:
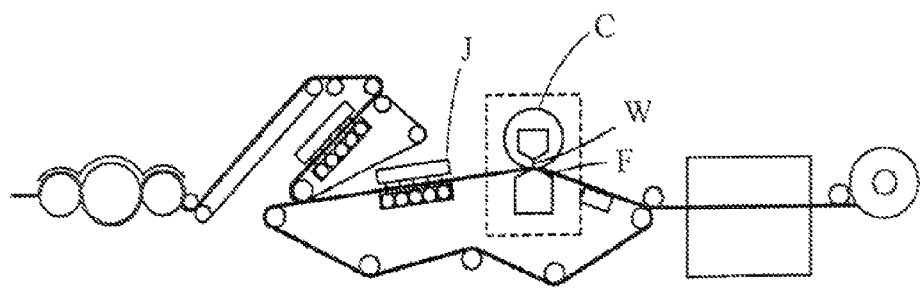
Figure 6E:
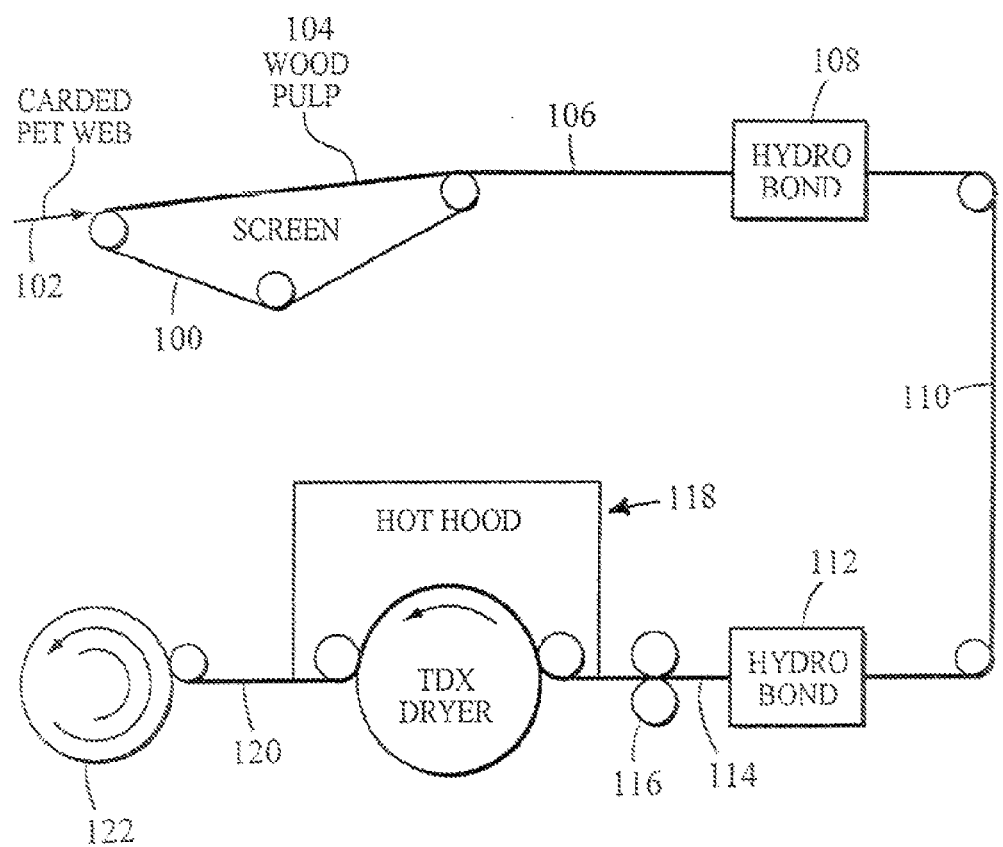
Figure 7:
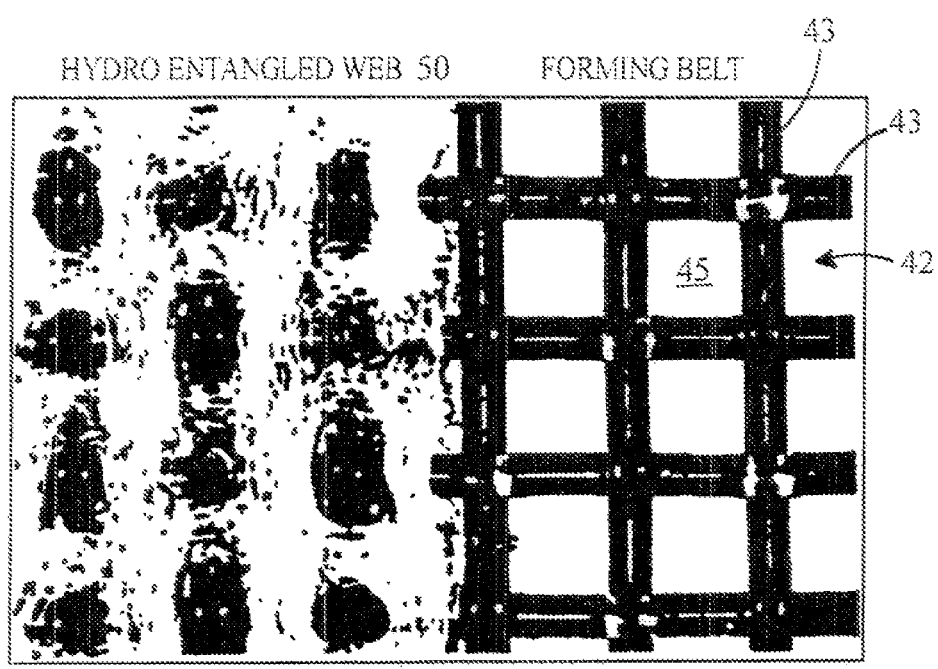
FIG. 7 diagrammatically illustrates a pre-formed hydroentangled product and the foraminous surface on which it is formed.

The general, presently preferred processes are illustrated in FIGS. 6-6E. The drawings of FIGS. 6A and 6B indicate that the basic elements of the spunlace process involve a webformer 40, a forming surface 42, in this case an open weave plastic or wire belt, high-pressure water jets 44, a dryer 46 and a windup station 58 for the hydroentangled pre-form product. In practice, web former 40, delivers, e.g., a dry formed web or a wet formed web of fibers as a loose pre-formed web or batt 41 onto the forming surface 42. While in contact with the forming surface, the web or batt is subjected to the high-pressure water jets. In some embodiments, such as the one illustrated in FIGS. 6 and 6B, vacuum boxes 47 are provided adjacent the forming surface on a side opposite water jets 44 to enhance the entangling energy applied to the web formation 41. In any event, the energy in the water stream displaces the fibers of the web or batt from the solid filaments 43 making up the forming surface 42 and works the fibers into the interstices 45 between the forming surface filaments, see FIG. 7. In the process, the force of the water also twists and entangles the fibers so that a strong integrated fabric 50 is obtained which may have the appearance of the reverse image of the forming belt or surface. Referring further to FIG. 7, the non-woven web 50 has been formed and water jet entangled on forming surface 42, e.g., an open weave belt.

In the early process known as the Evans process, as described in U.S. Pat. No. 3,485,706, textile-like non-woven fabrics were produced by traversing fibrous materials with high-energy liquid streams while the materials were supported on an apertured member such as a perforated plate or a woven wire screen. The action served to consolidate the material in a repeating pattern of entangled fiber regions and interconnecting fibers. With this process various types of fibers can be employed, for instance staple fiber and continuous filament. In the case of the present invention, the fibers are formed as a composite, including synthetic thermoplastic fibers and sorbent fibers. In general, in the early days, the preferred range of openness of the forming surface was considered to be between about 35 to 65 percent and the water pressure used was preferably in the range of 200 psi to 1200 psi (1.4 to 8.3 mPa). The orifice diameters for the water jets were recognized to lie in the range of between 0.003 inch and 0.030 inch (0.08 to 0.8 mm.) in diameter.

Another process known from the Honeycomb Systems Company is illustrated in FIG. 6C. This shows a web former, a drum entangling unit, a water extraction roll and a through air dryer. A honeycomb roll adds a support medium providing for a compact machine design with the option of entangling on both side of the web by employing two drum entanglers. A further advantage of the equipment lay in the fact that the high open area and rigid structure of the honeycomb shell provided support to the substrate while allowing the diffused water from the high pressure jets to pass through the shell to vacuum slots.

In the machine described in FIG. 6D known as the "Perfect Process", the web is first pre-entangled using water jets J and then a curtain of water W ranging from 3 to 8 mils in thickness is passed through a perforate cylinder C and through a fiber web F which is positioned on a backing belt. As the water curtain passes through the perforated cylinder, precise jets of water form and shape a pattern corresponding to the screen pattern. This patterned water screen rearranges the fiber webs to the screen pattern. The processes illustrated are further described in a technical paper, entitled "Spunlace Processes Worldwide," by Peter N. Britton, Ph.D., to which article the reader is referred.

In the embodiment of FIG. 6E a forming screen 100 receives a carded web 102 of PET fibers and an equal quantity of wood pulp 104, which is deposited upon carded web 102. This composite 106 is passed to a first hydrobond station 108 in which high-pressure water jets (not shown) cause entanglement of the wood pulp fibers with themselves and with the fibers of the thermoplastic strength web. The resulting web 110 is then in effect turned over and subjected to a second hydrobonding action at a second hydrobonding station 112, which further entangles the fibers making up the composite. From there the web 114 is passed to a squeeze nip 116 for removing excess water and then the composite is introduced to a heated drying 118 for removing the moisture and producing the dried hydroentangled web 120 which is wound in a reel 122 for further processing.

Figure 8:
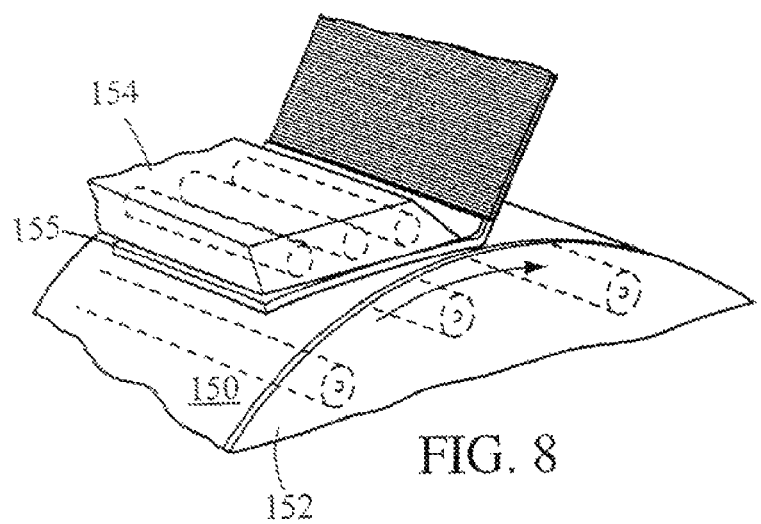
Figure 9:
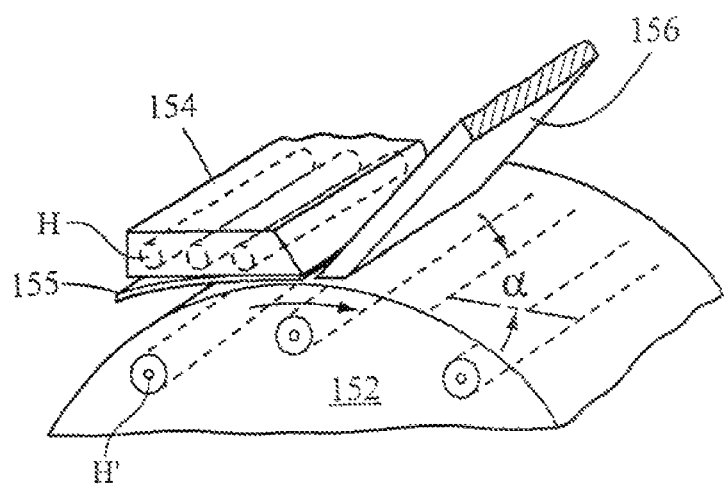
Figure 10:
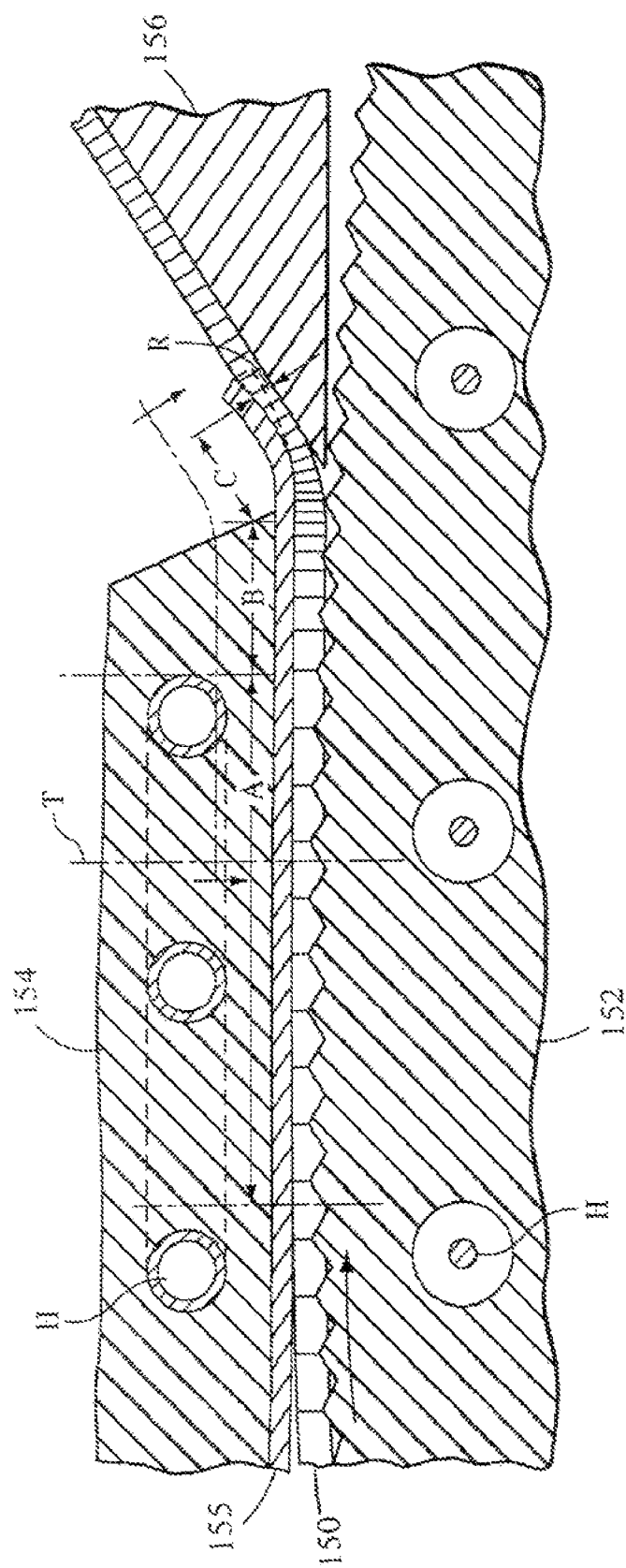
FIG. 10 illustrates, in highly magnified cross-section, machine components that apply heat during the processing of a fabric.

The presently preferred machine for conducting dry-creping of such preformed composite webs is described in U.S. Pat. No. 3,260,778, to which the reader is referred, some of the drawings of which are substantially reproduced in the present application as FIGS. 8-13. Referring to FIGS. 8, 9, 10 the composite hydroentangled web 150 is introduced to the drive roll 152 and under a stationary presser member 154, referred to in the patent as a "shoe," which has an underlying sheet member 155 that presses web 150 against the advancing drive roll 152 to cause the web to be driven forward towards a retarder element 156. The dimensions of the cavity formed by roll 152, sheet member 155 and retarder 156, see FIG. 13, further described below, are adjusted to a relatively wide final condition to enable the web to be coarsely folded upon itself by repeated columnar collapse of the sheet, to form the preferred coarse ridges and grooves that have been described. While the web receives no substantial squeezing pressure in the direction of its thickness, the web is dimensionally constrained, thickness-wise, to establish the coarseness of the dry-crepe.

Referring particularly to the diagram of FIG. 13, W indicates the nip thickness of the material, Y indicates the original thickness of the material Z, indicates the maximum separation of the divergent surfaces, R indicates the minimum separation of the surfaces of the retarding passage, referred to as the retarding restriction, θ indicates the obtuse angle between material on the moving surface as it approaches the retarding surface and the resultant of retarding forces imposed by the retarding passage at its retarding restriction R and Φ indicates the substantial acute angle included between retarding surface and the direction of movement of the traveling surface. The treatment cavity comprising zones B+C begins where the diverging walls are spaced apart a distance Y corresponding substantially to the original thickness of the material. The separation of the diverging surfaces increases progressively to its maximum dimension Z and then the cavity converges to the retarding restriction R. In operation the pile of micro condensed material extends through the obtuse angle θ back into the divergent passage from retarding restriction R, through the maximum dimension Z, thus longitudinally transmitting resistance forces from the retarding passage which oppose the fresh material forced forward into the divergent passage. Change in the retarder angle Φ changes the value of obtuse pile angle θ for any given relation of the other elements. With this preferred embodiment, in order to obtain the needed high resistance forces in the needed short length treatment cavity, and to obtain smooth movement of the material from the traveling surface to the retarder surface without cutting, the angle Φ must be substantial, and not highly acute. But if angle Φ is too great, then the pile of condensed material will buckle into the open "V" causing jamming of the machine or shearing of the material. Thus, angle Φ must be a substantial acute angle as noted above. For any given set of conditions there is generally found an optimum angle setting which cooperates with the force action of the other elements to obtain optimum micro condensing. It has been found that with changes in the total dimensions B+C to treat differing materials which involves substantial movement of the retarding surface relative to zone A, if the angle Φ remains constant, smooth flow of the material and proper transmittal of resistance by the pile results.

Substantially simultaneously with being dry-creped, heat is applied to web 150, for instance by heaters H associated with the presser member 154 and/or by heaters H' disposed in the driven roll 152. The heating mode may be any of the numerous known kinds, e.g., electric resistance, steam, hot water, hot gas or hot air. Radiant or flame pre-heating may also be employed. The heat thus imparted to the fabric cooperates with mechanical heat generated in the physical dry-creping action and the pressure applied to the sheet material in the directions of the plane of the material when the (preferably coarse) crepes are pushed against each other to effectively, permanently deform the thermoplastic constituents of the web to impart permanent ridges and grooves to the material that resist prolonged presence of wiping fluid.

After being so treated, the web is passed to station 15 (FIG. 1) where fabrication of the wet wipes is completed.

While the bladed drycreper shown in presently preferred, see U.S. Pat. No. 3,260,778, other dry-creping machines may be employed in appropriate instances, for instance those machines described in U.S. Pat. Nos. 3,810,280; 3,869,768; 3,975,806; 4,142,278; 4,894,196; 4,859,169 and 3,236,718, may also be employed. The reader is referred to each of these publications.

The adjustment of the retarder blade 156 back from the presser member 154 and its associated sheet member 155 is effective to open the dry-crepe cavity (FIGS. 9, 10, 13) to increase the size and decrease the frequency of the crepes.

Other alternative methods and apparatus suitable for carrying out the dry-creping process of the present invention are disclosed in Walton U.S. Pat. No. 2,915,109 and Packard U.S. Pat. No. 4,090,385, to which the reader is also referred. Briefly, these references show longitudinally compacting a web by feeding it over a roll that has alternating, circumferential ribs and grooves along its length. A flat shoe presses the web against the roll to enable the ribs of the roll to drive the web forward. Then a cylindrical comb (rotating with a peripheral speed lower than the roll) or a fixed comb (whose teeth mate with the grooves of the main roll) lifts the web from the main roll and at the same time compacts it longitudinally. In the latter case, a wide, flexible metal sheet extension from the shoe engages the face of the web opposite the web face that engages the retarder comb, to form with the retarder comb a confining passage for the creped material. These methods and apparatus are modified to provide the necessary heat to heat-set the thus dry-creped material.

Figure 11:
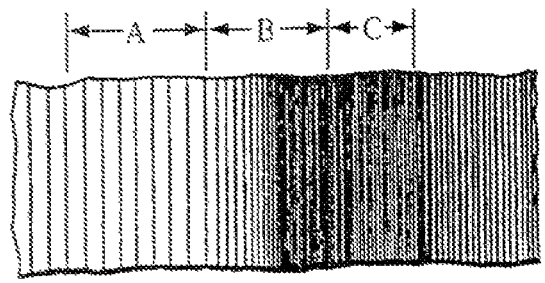
FIG. 11 illustrates shortening of the web as it passes through the drycreper.

Referring particularly to FIG. 11, the hydroentangled web 15 is compacted in the dry-creping process, zones B+C, so that an uncompacted region, zone A, is shortened. In some embodiments the percentage of compaction is between about 4% and 25%, i.e., a given portion of material following zone C occupies a length between about 75% and 96% the length it occupied in zone A. In other embodiments the percentage of compaction is between about 4% and 12%. In yet other embodiments the percentage of compaction is between about 4% and 8%. In yet another embodiments the residual compaction is negligible but the changes in thickness and internal volume, adsorbent capacity and the readsorption capacity are improved nonetheless.

Figure 14:
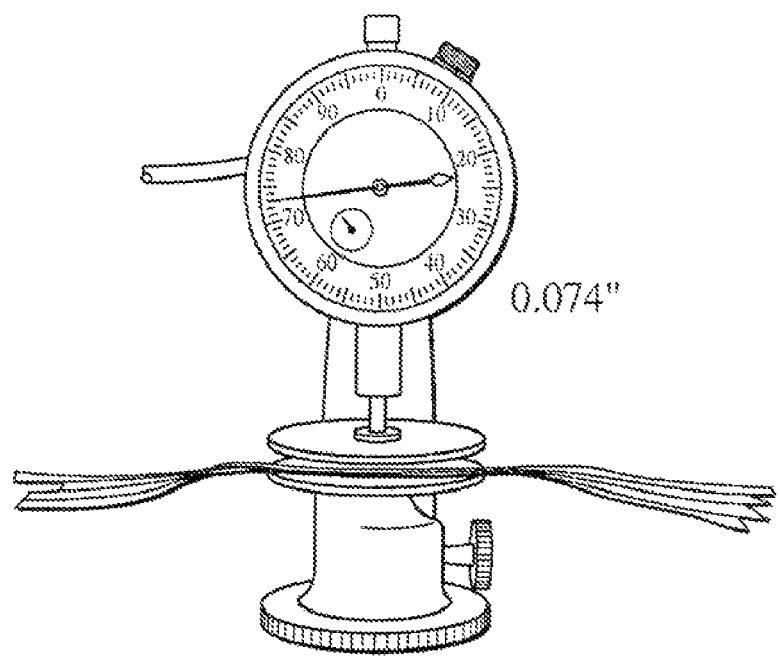
Figure 15:
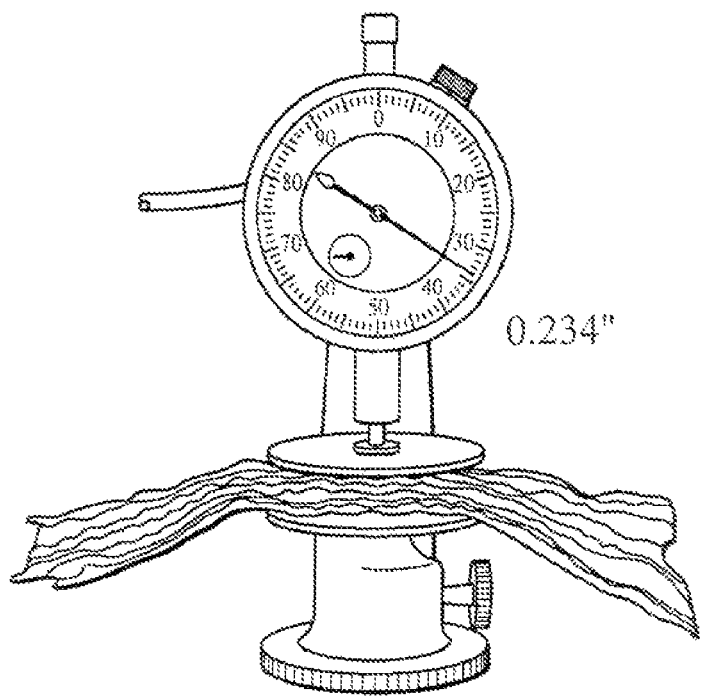
FIG. 15 shows the same device measuring a stack of the same number of sheets treated according to the invention.

Referring to FIGS. 14 and 15, dramatic results achieved by the invention are suggested by measuring a stack of wipe members with and without the heat-set dry-crepe treatment described (prior to application of the wet wiping agent).

Whereas the stack in FIG. 14 of eight untreated wipes measures 0.074 inch thickness, the stack of eight wipes with gross coarse dry-crepe in FIG. 15 measures 0.234 inch thickness (ridges are not aligned in adjacent sheets due to the slight randomness of the dry creping process). It is found that, with application of the wet wiping agent to, for instance, sheets of the preferred embodiment, the ridges in the sheet members of FIG. 15 are substantially preserved despite the tendencies of the pulp fibers to expand and straighten upon imbibing wiping liquid.

Each and every one of the above referenced publications is hereby fully incorporated by reference, including: U.S. Pat. Nos. 2,915,109; 3,236,718; 3,260,778; 3,485,706; 3,679,535; 3,679,536; 3,810,280; 3,869,768; 3,975,806; 4,090,385; 4,142,278; 4,894,196; 4,859,169; 5,240,764; 5,254,399; 5,227,224 and 5,284,703, GB Patent No. 2 114 173A and the technical paper entitled, "Spunlace Processes Worldwide," by Peter N. Britton, Ph.D., and the references cited in "Principles of Nonwovens" chapter 4 pages 539-641 edited by John E. Reidel, copyright 1993 by INDA, the association of the nonwovens industry, as well as the entirety of this book.

The following examples are provided and tested under the following conditions with the advantageous results noted.

Three different commercial materials were selected:

(1) A material known as JWS Fibrella No. 4300, from JWS in Spain, a 70 gram per square meter nonwoven material, the fiber content of which is 50% polyester fiber and 50% wood pulp, the nonwoven produced by the technique of hydroentanglement;

(2) A material known as an Orlandi nonwoven, produced by Orlandi, S A, of Varesi, Italy, characterized by a weight of 50 gram per square meter, the fiber content of which is 50% polypropylene fibers and 50% wood pulp, the nonwoven produced by the technique of hydroentanglement;

(3) A material known as Ahlstrom No. 962, a 60 gram per square meter nonwoven having a fiber content of 50% polyester fiber and 50% wood pulp, to which an acrylic latex binder of estimated 20% by weight has been added, the nonwoven material produced by a wet lay process.

Running lengths of each of these materials were subjected to microcreping using a commercial bladed microcreper, available from Micrex Corporation, Walpole, Mass., having a mechanical set up substantially as shown in FIG. 12. Active heating was provided only with an oil heated drive roll. Roll surface temperature was 365 F for the two materials containing polyester thermoplastic fibers and 270 F for the material containing the polypropylene fibers. The dimension Z (FIG. 13) was approximately 0.010 inch in each case. Each of the materials was treated employing a line speed of approximately 200 meter per minute, and the take-up speed of the machine was adjusted relative to the feed to produce compaction (shortening of the web length) at about the 15% level.

Absobency testing was conducted according to the INDA test method 10.1 (95) paragraph 8 (INDA is a trade association of the nonwovens industry, located in Cary, N.C.). Thickness was measured employing thickness gauge No. 202, available from the Ames Co., Beverly, Mass., using a 1⅞ inch diameter foot.

The results are given in the following table with respect to an individual wipe sheet of planar dimensions 4 inch width and 7 inch length. The absorbency tests were performed on stacks of sheet weighing 5 grams per stack (dry) according to the test methodolgy. Both dry and wet weights were calculated by dividing the stack weight by the number of sheets in the stack.

As the tables indicate, the dry density of the wipe sheets per unit area increased due to compaction by the microcreper in accordance with the approximate 15% compaction (shortening of the length) produced by the treatment.

The increase in dry thickness of the sheets, measured before the samples were saturated with water, however, ranged from 46% for the Orlandi fabric, 79% for the JWS Fibrella fabric to 250% for the Ahlstrom fabric.

The increase in wet weight of the non-creped and the microcreped wipes ranged from 22% for the Ahlstrom fabric, 32% for the Orlandi fabric and 41% for the JWS Fibrellas fabric, each indicating a significant increase in its liquid capacity.

| JWS Fibrella #4300, 70 gsm, 50% polyester/50 pulp (hydroentangled) | | | |
| --- | --- | --- | --- |
| Property | Non-Creped | Creped-15% Compaction | Change % |
| Weight - Dry (gms) | 1.344 | 1.564 | +16% |
| Thickness Dry (in) | 0.0123 | 0.0220 | +79% |

-continued

JWS Fibrella #4300, 70 gsm, 50% polyester/50 pulp (hydroentangled)

| Property | Non-Creped | Creped-15% Compaction | Change % |
|---|---|---|---|
| Weight - Wet (gms) | 6.08 | 8.60 | +41% |
| Thickness Wet (in) | 0.015 | 0.025 | +66% |

Orlandi 50 gsm 50% polypropylene/50 wood pulp (hydroentangled)

| Property | Non-Creped | Creped 15% Compaction | Change % |
|---|---|---|---|
| Weight - Dry (gms) | 0.95 | 1.11 | +17% |
| Thickness Dry (in) | 0.0150 | 0.0220 | +46% |
| Weight - Wet (gms) | 4.13 | 5.477 | +32% |
| Thickness Wet (in) | 0.013 | 0.018 | +38% |

Ahlstrom #962 60 gsm - 50% polyester/50% wood pulp (wet lay process + acrylic latex binder)

| Property | Non-Creped | Creped 15% Compaction | Change % |
|---|---|---|---|
| Weight - Dry (gms) | 1.0 | 1.16 | +16% |
| Thickness Dry (in) | 0.006. | 0.021 | +250% |
| Weight - Wet (gms) | 3.68 | 4.52 | +22% |
| Thickness Wet (in) | 0.0064 | 0.0146 | +128% |

Within the spirit and scope of the above teachings, numerous variations in the parameters, combinations and apparatus described are to be employed depending upon the specific products desired, and are within the following claims.

What is claimed is:

1. A method for manufacturing a wet wipe product comprising:

providing a continuous, preformed, nonwoven self-supporting sheet-form wet wiping web material constructed for a predetermined wet wiping task, at least 20% by weight of the wet wiping material comprising thermoplastic fibers, the thermoplastic fibers being of type, concentration and dispersion selected to be capable of being heat-set when the material is in a reformed shape to set the thermoplastic fibers and thereby the overall web material in the reformed shape, the web material comprising a fiber assemblage which includes a substantial proportion of wood pulp fibers, the fiber assemblage being substantially free of thermoplastic binder, forming, by dry creping action, a succession of ridges and grooves in the preformed wet wiping material by passing the material through a dry creper apparatus in the absence of an adhesive agent, the action characterized by pressing against one side of the material with a stationary pressing surface, to cause the opposite side of the material to engage with an advancing drive surface in the absence of adhesion to the advancing surface, and thereby driving the sheet material forward against previously dry creped material which has been retarded, to cause bodily collapse of the material into a succession of adjacent ridges and grooves that increase the volume of the overall material, the dry-creping being conducted in a manner leaving the wood pulp fibers substantially permanently uncompressed in the direction of the thickness of the assemblage, heating the wet wiping material to a temperature and in a manner sufficient to heat-set the dry-creped thermoplastic fibers and thereby the ridge and groove configuration of the overall material to enable the ridges and groove configuration to be preserved when the wet wiping material is wetted, and thereafter fabricating the continuous wet wiping material with its heat-set ridges and grooves into a series of wipe members for individual use.

2. The method of claim 1 in which the preformed nonwoven wet wipe sheet-form web material is selected to comprise between about 1/3 and 2/3 by weight of the thermoplastic fibers.

3. The method of claim 1 in which the preformed nonwoven wet wipe sheet-form web material is selected to comprise about one half by weight of the thermoplastic fibers.

4. The method of claim 1, 2 or 3 in which the thermoplastic fibers comprise PET (polyester).

5. The method of claim 1, 2 or 3 in which the thermoplastic fibers comprise polypropylene.

6. The method of claim 1, 2 or 3 in which the thermoplastic fibers comprise polyethylene.

7. The method of claim 1, 2 or 3 in which the preformed nonwoven wet wipe sheet-form web material is selected to include a substantial quantity of wettable fibers in an assemblage having substantial wicking capability, and the process is conducted in manner whereby the heat-set of the ridge and groove configuration enhances the recoverable internal volume of the wipe members.

8. The method of claim 1, 2 or 3 in which the preformed nonwoven wet wipe sheet-form web material is selected to include at least about 1/3 by weight of liquid absorbent or liquid adsorbent fibers.

9. The method of claim 1, 2 or 3 in which the preformed web material comprises a spunlace web.

10. A method for manufacturing a wet wipe product comprising:

providing a continuous, preformed, nonwoven self-supporting sheet-form wet wiping web material constructed for a predetermined wet wiping task, at least 20% by weight of the wet wiping material comprising thermoplastic fibers, the thermoplastic fibers being of type, concentration and dispersion selected to be capable of being heat-set when the material is in a reformed shape to set the thermoplastic fibers and thereby the overall web material in the reformed shape, forming, by dry creping action, a succession of ridges and grooves in the preformed wet wiping material by passing the material through a dry creper apparatus in the absence of an adhesive agent, the action characterized by pressing against one side of the material with a stationary pressing surface, to cause the opposite side of the material to engage with an advancing drive surface in the absence of adhesion to the advancing surface, and thereby driving the sheet material forward against previously dry creped material which has been retarded, to cause bodily collapse of the material into a succession of adjacent ridges and grooves that increase the volume of the overall material, heating the wet wiping material to a temperature and in a manner sufficient to heat-set the dry-creped thermoplastic fibers and thereby the ridge and groove configuration of the overall material to enable the ridges and groove configuration to be preserved when the wet wiping material is wetted, and thereafter fabricating the continuous wet wiping material with its heat-set ridges and grooves into a series of wipe members for individual use, the prefomed web material comprising spunlace web formed by providing a carded web of polyester fibers, introducing a layer of wood pulp to the carded web, and subjecting the layer of wood pulp and carded web to hydroentanglement followed by dewatering and drying to form the self-supporting sheet-form web material for introduction to the dry-creping.

11. The method of claim 1 in which the preformed continuous nonwoven sheet-form wet wiping web material is fabricated at least in part by the process of thermal bonding, chemical bonding, spun bonding, melt blowing, caustic entangling, hydraulically aperturing, hydro-entangling, wet laying or papermaking.

12. The method of claim 1 or 10 conducted in the manner to form the ridges at frequency between about 8 and 25 ridges per lineal inch.

13. The method of claim 12 conducted in the manner to form ridges at frequency between about 8 and 15 ridges per lineal inch, defining wipe-stress concentrating edge useful, for instance, for vigorous wiping action.

14. The method of claim 12 conducted in the manner to form ridges at frequency between about 15 and 20 ridges per lineal inch, defining wipe-stress concentrating edges.

15. The method of claim 1 or 10 including stacking a series of wet wipe members face-to-face in a stack, with substantial non-alignment between ridges and grooves in successive members in the stack.

16. The method of claim 15 including inserting the stack into a package.

17. The method of claim 16 in which the package is liquid tight and a liquid agent is included with the wet wipe members in the package.

18. The method of claim 17 in which the liquid agent comprises at least one of a soap, a detergent, a solvent, a cleaning agent, a window washing agent, a sanitizing agent, a biocide, a polishing agent, an abrading agent or a neutralizing agent.

19. The method of claim 17 in which the liquid agent comprises at least one of an insect repellant, a paint solvent, a paint remover, a finish remover, an oil solvent, a grease solvent, a cosmetic remover, a makeup remover, a stain remover, a stain, a paint, a varnish, a wax or a polish.

20. A wet wiping member produced by the method of claim 1.

21. A wet wiping member produced by the method of claim 7 or 16.

22. The method of claim 10 in which the preformed nonwoven wet wipe sheet-form web material is formed to comprise between about 1/3 and 2/3 by weight of the thermoplastic fibers.

23. The method of claim 10 in which the preformed nonwoven wet wipe sheet-form web material is foamed to comprise about one half by weight of the thermoplastic fibers.

24. A wet wiping member produced by the method of claim 10.

\* \* \* \* \*

UNITED STATES PATENT AND TRADEMARK OFFICE
CERTIFICATE OF CORRECTION

PATENT NO. : 7,767,058 B2  Page 1 of 1
APPLICATION NO. : 11/688853
DATED : August 3, 2010
INVENTOR(S) : Richard C. Walton, Peter R. Smith and Drew Horn It is certified that error appears in the above-identified patent and that said Letters Patent is hereby corrected as shown below:

Column 17, line 8, "prefomed" should be -- preformed --.

Column 18, line 21, delete "or 16".

Column 18, line 27, "foamed" should be -- formed --.

Signed and Sealed this

Seventh Day of December, 2010

David J. Kappos
*Director of the United States Patent and Trademark Office*